United States Patent [19]

Holzwarth

[11] Patent Number: 4,730,726

[45] Date of Patent: Mar. 15, 1988

[54] SEALED STERILE PACKAGE

[75] Inventor: Henry A. Holzwarth, Weston, Conn.

[73] Assignee: United States Surgical Corporation, Norwalk, Conn.

[21] Appl. No.: 40,924

[22] Filed: Apr. 21, 1987

[51] Int. Cl.$^4$ .............................................. B65D 81/26
[52] U.S. Cl. ..................... 206/204; 206/230; 206/339; 206/471; 206/484.1; 206/524.2; 206/524.8
[58] Field of Search ............... 206/484.1, 524.2, 524.8, 206/204, 230, 339, 471, 363; 53/400, 403, 408, 427

[56] References Cited

U.S. PATENT DOCUMENTS

| | | | |
|---|---|---|---|
| 3,861,529 | 1/1975 | Coleman | 206/471 |
| 3,910,410 | 10/1975 | Shaw | 206/471 X |
| 4,412,617 | 11/1983 | Cerwin | 206/204 X |
| 4,482,053 | 11/1984 | Alpern et al. | 206/484.1 X |
| 4,497,406 | 2/1985 | Takanashi | 206/524.2 X |
| 4,519,501 | 5/1985 | Cerwin | 206/204 X |

Primary Examiner—William Price
Attorney, Agent, or Firm—Kenyon & Kenyon

[57] ABSTRACT

The sealed package is sterilized with a sterilant gas such as ethylene oxide prior to application of a desiccant pack. The desiccant pack is applied after sterilization and held in place by a metallic foil which is impermeable to moisture. A moisture permeable layer separates the desiccant pack from the plastic tray-like layer in which the surgical instrument is disposed. Absorbable co-polymer staples are maintained moisture-free by virtue of the desiccant pack being located on the opposite side of the moisture permeable layer.

16 Claims, 5 Drawing Figures

U.S. Patent   Mar. 15, 1988   Sheet 2 of 2   4,730,726
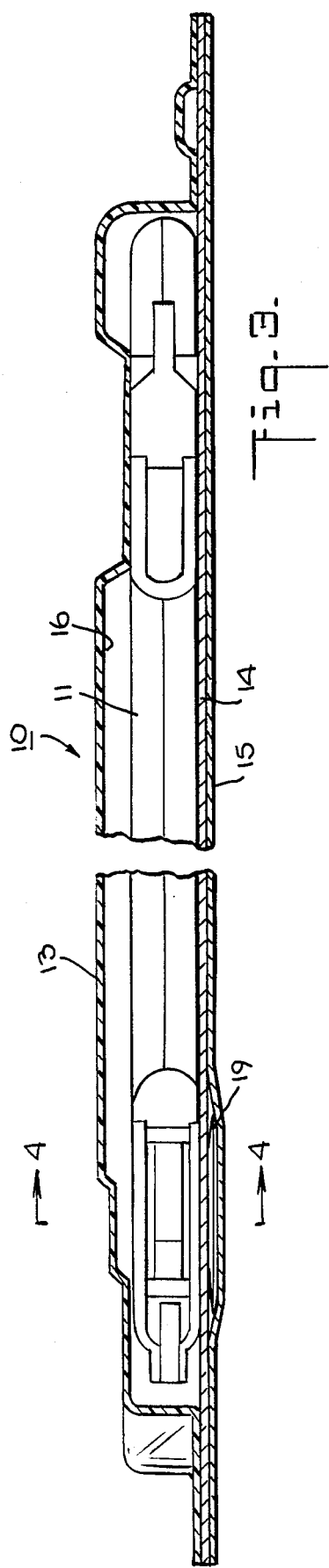
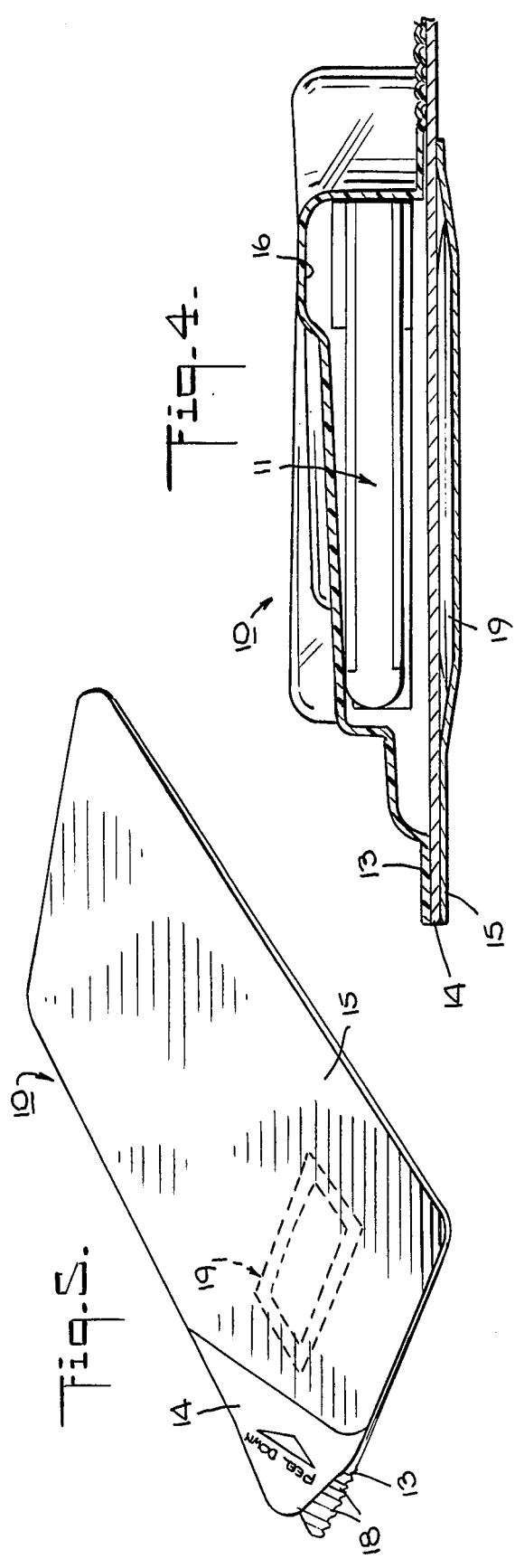

SEALED STERILE PACKAGE

This invention relates to a sealed sterile package. More particularly, this invention relates to a sterile package for surgical instruments.

As is known, surgical instruments are frequently packaged in a sterilized condition for a single use. That is, the instruments are intended to be of a disposable nature. In the past, various techniques have been known for sterilizing the instruments before or after being packaged.

In the case of surgical instruments which are made with moisture sensitive components, such as surgical staplers having absorbable copolymer staples which are subject to hydrolytic degradation, sterilizing with steam is not practicable due to the moisture and heat sensitivity of such polymers. Thus, instruments which include components made of such polymers are usually sterilized using a sterilant gas such as ethylene oxide.

In the use of ethylene oxide, sterilization can be enhanced by the presence of moisture vapor. A typical sterilization procedure employing ethylene oxide may maintain a relative humidity of about 40% to 50% within the package in a sterilization chamber during sterilization. However, this moisture is absorbed and retained to some extent by the instrument and the interior of the package. Hence, the moisture must be substantially removed in order to produce a packaged instrument in which the polymer component contains its integrity even after prolonged storage. Accordingly, following sterilization, such packages have typically been evacuated in order to remove the sterilant gas while also removing or reducing the moisture content of the interior of the package. However, the moisture content has frequently not been reduced to an acceptable level for prolonged storage. Accordingly, proposals have been made to include a desiccant material within the package which will establish an equilibrium moisture content of the polymer after sterilization, evacuation and sealing of the package which is at a pre-selected value acceptable for prolonged storage. However, it has been found that the materials which have been used for the desiccant may react with the sterilizing gas to give a toxic reaction.

Accordingly, it is an object of the invention to provide a sealed sterile package for surgical instruments having moisture sensitive components which can be maintained in a substantially moisture free state.

It is another object of the invention to be able to use a desiccant material in a sterilized package which has been sterilized with a sterilizing gas.

It is another object of the invention to provide a relatively simple package for maintaining instruments in a sterilized moisture-free state.

Briefly, the invention provides a sealed sterile package containing a sterilized surgical instrument having a moisture-sensitive component. The package includes a formed plastic layer having at least one recess receiving the instrument, a moisture permeable layer secured to the plastic layer about the recess, a desiccant pack disposed on a side of the permeable layer opposite the plastic layer and adjacent to the moisture-sensitive component and a moisture impervious layer secured to the permeable layer to encase the desiccant pack therebetween.

In order to sterilize the package, the surgical instrument is first placed within the recess of the plastic laye and the moisture permeable layer is secured to the plastic layer about the recess. Thereafter, a sterlization process can be performed, for example, using a sterilant gas such as ethylene oxide. During this time, the sterlizing gas permeates through the moisture permeable layer into the interior of the package in order to sterilize the instruments. After completion of the sterilization process, the remainder of the package can be fabricated. That is, the desiccant pack can be disposed on the permeable layer opposite the moisture-sensitive component of the instrument and the moisture impervious layer secured in place. Thereafter, the completed package can be shipped or otherwise transported to a storage site for subsequent use.

When the package is to be utilized, for example in an operating room, an appropriate attendant removes the permeable layer together with the moisture impervious layer from the plastic layer in order to expose the surgical instrument. To this end, the package can be constructed so that the moisture impervious layer exposes a portion of the permeable layer with this exposed portion being unsecured to the plastic layer. In this way, a flap is formed which can be readily separated from the plastic layer, for example at a corner of the package in order to enhance peeling of the permeable layer from the plastic layer.

The plastic layer can be made of any suitable material and may be formed in the manner of a tray-like structure so as to receive a surgical instrument.

The surgical instrument may be made with one or more moisture=sensitive components. For example, where the surgical instrument is in the form of a surgical stapler, the components may be in the form of staples which are made of a polymer subject to hydrolytic degradation.

The moisture permeable layer may be made of any suitable material. For example, the preferred material is one which is permeable to moisture vapor and sterilant gas while being impervious to microorganisms. Such a material is a spun bonded olefin, such as a high density polyethylene fabricated by an intergrated spinning and bonding process which is available commercially from the DuPont Chemical Company under the trademark TYVEK.

The desiccant which is used may be made of any suitable materials. For example, the desiccant may be selected from the group consisting of silica gel, molecular sieves, activated alumina, porous silica glass and mixtures thereof. Further, the desiccant may be contained within a pouch of moisture permeable polymeric material.

These and other objects and advantages of the invention will become more apparent from the following detailed description taken in conjunction with the accompanying drawings wherein:

FIG. 3 illustrates a cross sectional view of the package of FIG. 1;

FIG. 4 illustrates a further cross sectional view of the package taken on line IV—IV of FIG. 3; and FIG. 5 illustrates a bottom view of the package of FIG. 1.

Figure 1:
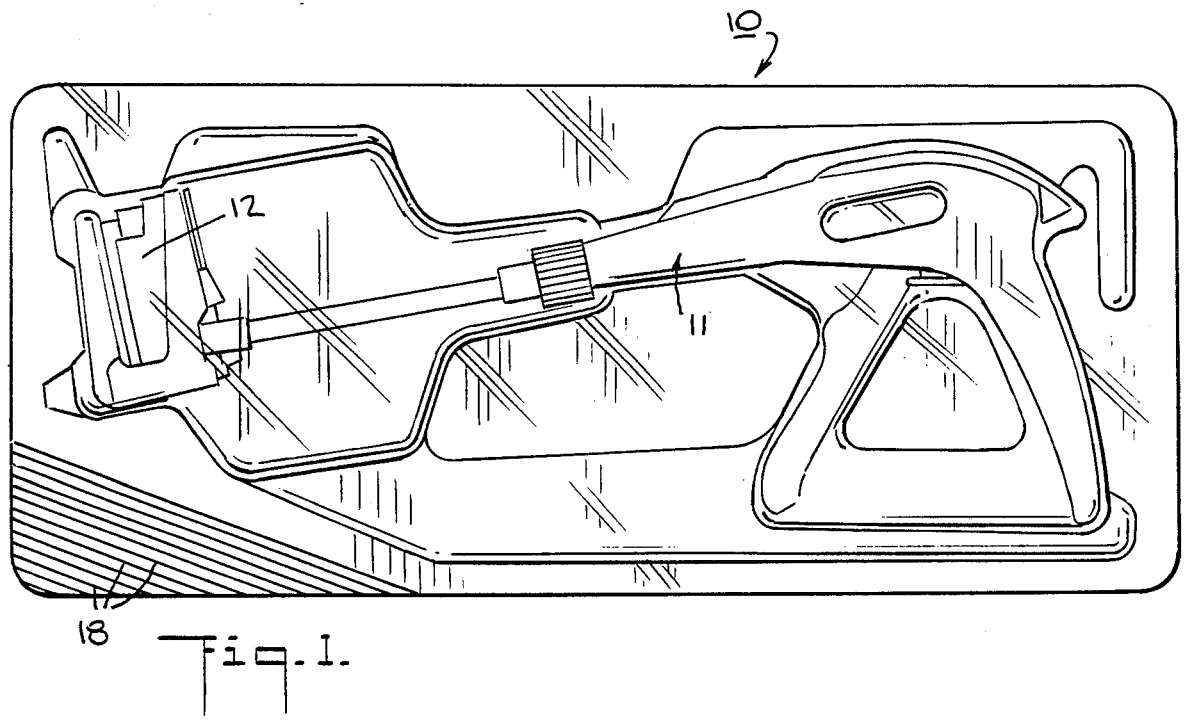
FIG. 1 illustrates a plan view of a sealed sterile package in accordance with the invention.
Figure 2:
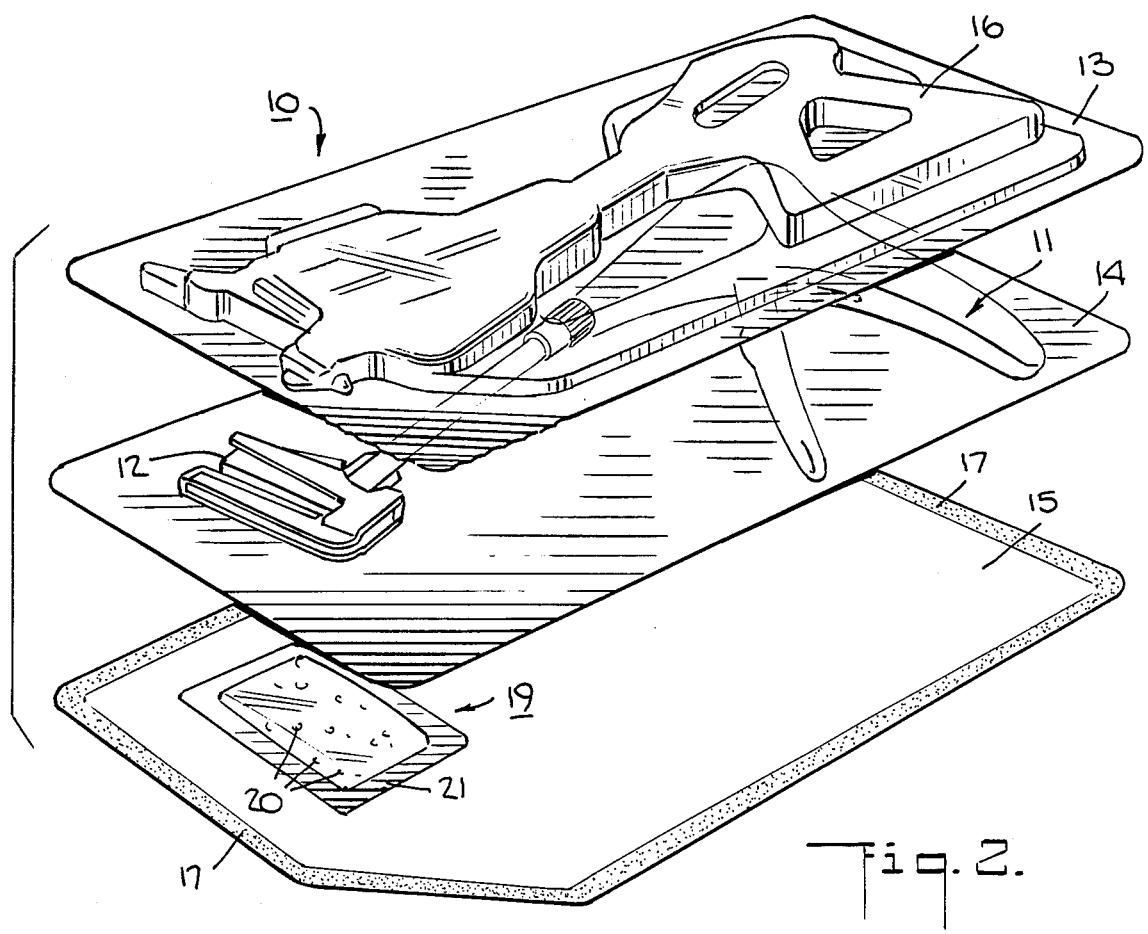
FIG. 2 illustrates an exploded view of the package of FIG. 1.

Referring to FIGS. 1 and 2, the sealed sterile package 10 is constructed so as to contain a surgical instrument 11, for example, a surgical stapler having moisture-sensitive components. For example, the instrument 11 has a cartridge 12 at a distal end which contains a plurality of surgical staplers made of a polymer which is subject to hydrolytic degradation. For example, the cartridge 12 contains absorbable polymer staples made of a polyester derivative of lactic and glycolic acids.

The package 10 includes three layers 13, 14, 15. The top layer 13, as viewed, is a preformed plastic layer which is made of a suitable plastic material and which is formed with at least one recess 16 for receiving the surgical instrument 11. As indicated in FIG. 2, the recess 16 is of the general contoured shape of the instrument 11. Further, the layer 13 is made of transparent material so that the packaged instrument 11 can be readily viewed.

The middle layer 14 is a moisture permeable layer which is secured to the plastic layer 13 about the recess 16. In this respect, suitable lines of glue or adhesive (not shown), such as a heat sealable adhesive, are used to secure the permeable layer 14, directly to the plastic layer 13 to provide a seal-tight seam. Further, the glue or adhesive which is used is such that the permeable layer 14 is releasably secured to the plastic layer so that the permeable layer 14 can be subsequently removed when desired, for example, by peeling of the permeable layer 14 from the plastic layer 13.

The permeable middle layer 14 is characterized in being made of a material which is permeable to moisture vapor and sterilant gas while being impervious to microorganisms. Such a material can be a spun-bonded olefin such as a high density plyethylenefabricated by an intergrated spinning and bonded process which is available commercially from the DuPont Chemical Company under the trademark TYVEK. Other equivalent materials may also be employed provided they are permeable to moisture vapor and sterilant gas and impermeable to microorganisms.

The bottom layer 15 is made of a moisture impervious material such as a metallic foil, for example, aluminum foil. As indicated in FIG. 2, the moisture impervious layer 15 is secured to and across the permeable layer 14 via a line of adhesive or glue 17. As indicated in FIGS. 2 and 5, the moisture impervious layer 15 is secured only to a major portion of the permeable layer 14 in order to expose a portion of the permeable layer, for example, at one corner, to facilitate peeling of the permeable layer 14 from the plastic layer 13. In addition, the permeable layer 14 is unsecured to the plastic layer 13 within this exposed portion and the plastic layer 13 is provided with a plurality of ribs or corrugations 18 to facilitate peeling back of the corner of the permeable layer 14 when the package is to be opened.

The package also includes a desiccant pack 19 which is disposed between the permeable layer 14 and the impervious layer 15. As indicated in FIGS. 2, 3 and 4, the desiccant pack 19 is disposed adjacent to the moisture-sensitive component 12 of the surgical instrument 11, i.e. on a side of the permeable layer 14 opposite from the plastic layer 13 and instrument 11. The desiccant pack 19 includes a desiccant 20, for example, selected from the group consisting of silica gel, molecular sieves, activated alumina and porous silica glass. In addition, the desiccant is encased within a pouch of moisture permeable polymeric material.

As indicated in FIGS. 3 and 4, the desiccant pack 19 is of a size which is suitable to the size of the cartridge 12. In this respect, the pack 19 need not be fixedly secured in place but need only be placed on the permeable layer 14 prior to fixing of the impervious layer 15 to the permeable layer 14.

In order to sterilize the instrument 11, the instrument 11 is first placed within the recess 16 of the tray-like layer 13 and the permeable layer 14 is secured to the plastic layer 13 in sealed manner. In this regard, any suitable technique may be used to affix the permeable layer 14 to the plastic layer 13. Thereafter, the partially completed package is then subjected to a sterilizing process, for example, one in which a sterilizing gas such as ethylene oxide is caused to permeate through the permeable layer 14 into the interior of the package in order to sterilize the instrument 11. Thereafter, with the sterilant gas being completely and substantially completely removed, the sterilant pack 19 is placed down on the permeable layer 14 in the area of the cartridge 12 and the impervious layer 15 affixed in place. Again, any suitable technique may be used for affixing the impervious layer, i.e. aluminum foil, to the pervious layer 14.

The sterilized package can then be shipped to a suitable point of use or held in storage until ready for use.

When the package is to be opened, the user simply pulls back the exposed corner of the permeable layer 14 from the plastic layer 13 and then peels the permeable layer 14 together with the aluminum foil layer 15 from the plastic layer 13 until the instrument 11 has been sufficiently exposed for removal.

During storage, any moisture which may tend to collect within the interior of the package is permeated through the permeable layer 14 into the desiccant 20 of the desiccant pack 19. Thus, the desiccant 20 serves to maintain the interior of the package 10 in a relatively dry state. Further, since the desiccant pack 19 is not applied until after the sterilization process, the danger of a sterilant gas forming a toxic reaction with the desiccant material during sterilization is eliminated.

The invention thus provides a sealed sterile package of relatively simple construction for maintaihing surgical instruments having moisture-sensitive components in a relatively dry state.

The invention further provides a sterile package which can be made moisture-proof without creating a toxic condition between a sterilant gas and a desiccant.

What is claimed is:

1. A sealed sterile package comprising
    a sterilized surgical instrument having a moisture-sensitive component;
    a formed plastic layer having at least one recess receiving said instrument therein;
    a permeable layer secured to said plastic layer about said recess;
    a desiccant pack disposed on a side of said permeable layer opposite said plastic layer and adjacent said moisture-sensitive component of said instrument; and
    a moisture impervious layer secured to said permeable layer to encas said desiccant pack therebetween.

2. A sealed sterile package as set forth in claim 1 wherein said permeable layer is releaseably secured to said plastic layer for removal therefrom.

3. A sealed sterile package as set forth in claim 2 wherein said moisture impervious layer is secured to a major portion of said permeable layer to expose a portion of said permeable layer for peeling of said permeable layer and said moisture impervious layer from said plastic layer.

4. A sealed sterile package as set forth in claim 3 wherein said plastic layer has a corrugated portion opposite and unsecured to said exposed portion of said permeable layer.

5. A sealed sterile package as set forth in claim 1 wherein said component of said instrument is a cartridge of absorbable copolymer staples.

6. A sealed sterile package as set forth in claim 1 wherein said permeable layer is permeable to moisture vapor and sterilant gas and impervious to microorganisms.

7. A sealed sterile package as set forth in claim 6 wherein said permeable layer is made of spun-bonded olefin.

8. A sealed sterile package as set forth in claim 1 wherein said moisture impervious layer is a metal foil.

9. A sealed sterile package comprising
 a sterilized surgical instrument having at least one component made of a polymer subject to hydrolytic degradation;
 a formed plastic layer having at least one recess receiving said instrument;
 a moisture permeable layer secured to said plastic layer about said recess;
 a moisture impervious layer secured to and over said permeable layer; and
 a desiccant disposed between said permeable layer and said impervious layer opposite said component of said instrument.

10. A sealed sterile package as set forth in claim 9 wherein said permeable layer is releaseably secured to said plastic layer to be peeled therefrom.

11. A sealed sterile package as set forth in claim 9 wherein said moisture impervious layer is secured to a major portion of said permeable layer to expose a portion of said permeable layer for peeling of said permeable layer and said moisture impervious layer from said plastic layer.

12. A sealed sterile package as set forth in claim 9 wherein said component is an absorbable copolymer staple.

13. A sealed sterile package as set forth in claim 9 wherein said permeable layer made of spun-bonded olefin.

14. A sealed sterile package as set forth in claim 13 wherein said impervious layer is a metal foil.

15. A sealed sterile package as set forth in claim 9 which further comprises a pouch of moisture permeable polymeric material encasing said desiccant.

16. A sealed sterile package as set forth in claim 15 wherein said desiccant is selected from the group consisting of silica gel, molecular sieves, activated alumina and porous silica glass.

* * * * *

UNITED STATES PATENT AND TRADEMARK OFFICE
CERTIFICATE OF CORRECTION

PATENT NO.   : 4,730,726

DATED        : March 15, 1988

INVENTOR(S)  : HENRY A. HOLZWARTH

It is certified that error appears in the above-identified patent and that said Letters Patent is hereby corrected as shown below:

```
Column 1, line 30 "contains" should be -maintains-
Column 1, line 68 "laye" should be -layer-
Column 2, line 31 "moisture=sensitive" should be -moisture-
     sensitive-
Column 3, line 31 "plyethylenefabricated" should be -polyethylene
     fabricated-
Column 4, line 39 "maintaihing" should be -maintaining-
Column 4, line 58 "encas" should be -encase-
Column 6, line 17 "layer made" shoudl be -layer is made-
```

Signed and Sealed this

Eleventh Day of October, 1988

*Attest:*

DONALD J. QUIGG

*Attesting Officer*  *Commissioner of Patents and Trademarks*